United States Patent [19]

Huynh-Ba

[11] Patent Number: 5,401,858
[45] Date of Patent: * Mar. 28, 1995

[54] PREPARATION OF QUINIC ACID DERIVATIVES

[75] Inventor: Tuong Huynh-Ba, Pully, Switzerland

[73] Assignee: Nestec S.A., Vevey, Switzerland

[*] Notice: The portion of the term of this patent subsequent to Mar. 7, 2012 has been disclaimed.

[21] Appl. No.: 95,873

[22] Filed: Jul. 21, 1993

[30] Foreign Application Priority Data

Aug. 3, 1992 [EP] European Pat. Off. ............ 92113190

[51] Int. Cl.⁶ .................................................. C07D 307/00
[52] U.S. Cl. ...................................... 549/302; 562/508
[58] Field of Search ........................... 549/302; 502/508

[56] References Cited

U.S. PATENT DOCUMENTS 3,855,297 12/1974 Diana et al. .......................... 562/508
4,818,767 4/1989 Rossigual ............................ 562/508
4,940,803 7/1990 Mills et al. ............................ 549/302

FOREIGN PATENT DOCUMENTS 0802668 10/1958 United Kingdom .
8601508 3/1986 WIPO .

OTHER PUBLICATIONS

Ichikawa et al. CA 116 (23) 2360952 1992.
Haslam, et al., "Synthesis and Properties of Some Hydroxycinnamoyl Esters of Quinic Acid," J. Chem. Soc., pp. 2137–2146 (1964).
Wynne, et al., Chemical Abstracts, vol. 106, No. 9, No. 64477A (1986).
Ichikawa et al., Chemical Abstracts, vol. 116 No. 23 No. 2360952 (1992).

Primary Examiner—C. Warren Ivy
Assistant Examiner—A. A. Owens
Attorney, Agent, or Firm—Vogt & O'Donnell

[57] ABSTRACT

3- or 4-mono-, 1,3- or 1,4- or even 3,4-disubstituted derivatives of quinic acid are produced by reaction of a hydroxycinnamic acid derivative, of which the phenol group(s) is/are protected with a quinic acid derivative, to form an ester and the different reactivities of the OH functions in the 3 and 4 positions are used to carry out the esterification selectively under low temperature conditions, after which the protective groups are cleaved under controlled acidity and temperature conditions. These conditions avoid any degradation or isomerization. The process enables new quinides to be obtained in high yields.

9 Claims, No Drawings

PREPARATION OF QUINIC ACID DERIVATIVES

BACKGROUND OF THE INVENTION

This invention relates to new 3- and/or 4-substituted derivatives of quinic acid and to a process for their production.

Derivatives of quinic acid are widespread in the vegetable world. The chlorogenic acid content of green coffee beans, for example, can represent up to 10% of the dry matter. The term "chlorogenic acid" in fact encompasses a relatively complex mixture of quinic acid derivatives, including caffeoyl, dicaffeoyl, p-coumaroyl, feruloyl and caffeoylferuloyl quinic acids. After roasting, the coffee grains contain an even more complex mixture of compounds of which some are formed by lactones of quinic acids known as quinides or even other isomers formed during the heat treatment. Some of these derivatives show antimicrobial activity, opiate antagonistic activity, anti-inflammatory activity, fungistatic activity, cytostatic activity and inhibiting activity in the biosynthesis of leucotrienes. Applicants have found that some of these compounds show anti-urease activity, their use being the subject of a copending application filed by applicants under the title "An Anti-Urease Cosmetic or Dermatological Composition".

The synthesis of hydroxycinnamoyl quinic acids is described, for example, by E. Haslam et al. in J. Chem. Soc. 1964, 2137-2146. However, the known processes involve a delicate and laborious separation step based on the technique of countercurrent distribution in order to isolate the required compound in cases where the key esterification step is not regioselective and leads to an isomer mixture which has to be separated. In addition, the known method uses protective groups for the hydroxycinnamic reactants which can only be cleaved under drastic conditions (strong acid or strong base and heat), resulting in isomerization of the chlorogenic derivatives.

SUMMARY OF THE INVENTION

The present invention relates to new 3- and/or 4-substituted derivatives of quinic acid, namely quinides corresponding to the following general formula:

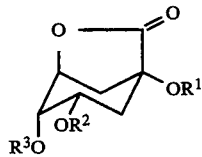

in which $R^1$ is H and one of the two groups $R^2$ and $R^3$ or both the groups $R^2$ and $R^3$ represent a group corresponding to the following formula:

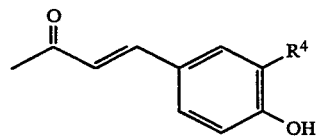

and $R^4$ represents H, $OCH_3$ or OH, $R^2$ being different from $R^3$, or is a group corresponding to the formula:

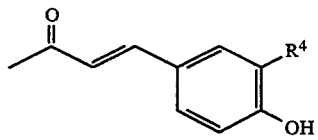

in which $R^4$ is as defined above and one of the two groups $R^2$ and $R^3$ is H and the other is a group corresponding to the formula:

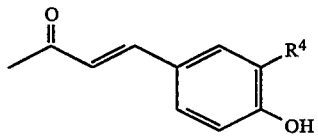

in which $R^4$ is as defined above.

The new compounds according to the invention are very useful intermediate products for the production of quinic acids having the interesting applications mentioned above.

In addition, 3-O-caffeoyl and 3-O-p-coumaroyl quinide show a negative inotropic effect. In vitro inhibition of the beta-adrenergic receptors has been observed in the case of 3-O-caffeoyl quinide in a dose of 5 microg/ml.

The present invention also relates to a process for the production of 3- and/or 4-substituted quinic acid derivatives, in which the substituent in the 3 position is different from the substituent in the 4 position and in which a derivative of a hydroxycinnamic acid, of which the hydroxyl group(s) is/are protected, is reacted with a protected derivative of quinic acid to form an ester and the protective group(s) is/are subsequently cleaved. This process is characterized in that the quinic acid derivative used is a quinide, in that the esterification or the introduction of a protective group in the case of the 4-substituted derivatives is carried out regioselectively in the 3 position of the quinic acid skeleton at a temperature below $-10°$ C., in that the protective groups are cleavable under controlled acidity and temperature conditions and in that, when it is desired to prepare the final quinic acid, the quinide is subjected to a acidic hydrolysis under controlled conditions, the controlled conditions enabling any degradation or isomerization to be avoided.

DETAILED DESCRIPTION OF THE INVENTION

In a first embodiment of the process according to the invention, monosubstituted 3-O-hydroxycinnamoyl derivatives of the quinide are prepared in high yields and are then converted into quinic acid. To this end, the OH functions in the 3, 4 and 5 positions and the carboxyl function in the 1 position of the quinic acid are protected, for example by reaction with acetone in the presence of p-toluene sulfonic acid, which leads to 3,4-O-isopropylidene quinide. A protective group is then introduced into the 1 position in the form of a carbonate, for example trichloroethyl carbonate, which may be cleaved under moderate conditions, for example with zinc in acetic medium at ambient temperature. Before cleavage of the protective carbonate in the 1 position, the acetonide group protecting the OH functions in the 3 and 4 positions of the quinide has to be released. A highly concentrated aqueous solution of trifluoroacetic acid at ambient temperature is used for this purpose. After the 3 and 4 positions have been released, the 3 position is selectively esterified by making use of the fact that the OH group in the 3 position has an equatorial conformation of which the substitution is more stable than that of the OH group in the 4 position of axial configuration providing the energy of the reaction is properly controlled. It is thus possible selectively to introduce a p-coumaryl or feruloyl substituent from a reactive derivative of the corresponding acid such as, for example, the chloride or anhydride, by carrying out the reaction at a temperature of < to −10° C. and preferably at a temperature of the order of −40° C. This is because it has been found that, at a temperature of > to −10° C., the ester in the 4 position is concomitantly formed. After cleavage of the carbonate protecting the 1 position under controlled conditions, for example with zinc in acetic acid at ambient temperature, the 3-substituted quinides are obtained. The controlled conditions mentioned above make it possible to avoid the decomposition which would occur under the conventional conditions where acetic acid is used at high temperatures.

Finally, in one variant of this embodiment intended for the preparation of substituted 3-caffeoyl derivatives, methyl carbonate is used as the protective group for the phenol functions of the caffeic acid. After the reaction, the trichloroethyl carbonate protective group is cleaved with zinc in the presence of acetic acid, after which the methyl carbonate groups are cleaved with lithium chloride in pyridine in the presence of chlorotrimethyl silane. The function of the chlorotrimethyl silane is to prevent migration of the caffeoyl radical from the 3 position to the 4 position of the quinic acid skeleton. Finally, to prepare the quinic acids corresponding to the quinides, the quinides are subjected to acidic hydrolysis, again under controlled conditions, for example with a catalytic quantity of p-toluene sulfonic acid in the case of the 3-p-coumaroyl and 3-feruloyl derivatives. In the case of the 3-caffeoyl derivatives, opening of the lactone ring of the quinide, for example with aqueous hydrochloric acid in the presence of a polar solvent, for example tetrahydrofuran, can only take place after all the hydroxy groups have been completely protected, for example by trichloroethyl carbonate groups, which may then be cleaved, for example with zinc in acetic acid.

In a second embodiment of the process according to the invention for the preparation of 4-monosubstituted derivatives of quinic acid, use is made of the above method of selective esterification of the quinide in the 3 position by introducing a trichloroethyl carbonate protective group into that position. The protected quinide is then used as starting material for esterification of the only OH function which is still free (in the 4 position) by a reactive derivative, for example an anhydride or a chloride of an acid of which the phenol functions have also been protected as described above. The various protective groups are then successively cleaved as described above and, if necessary, the quinide is subjected to acidic hydrolysis to form the corresponding quinic acid. It is important for this hydrolysis to ensure that there is no isomerization of the acyl quinic acids between the 3 and 4 positions, in which case all the benefit of the selectivity of esterification in the 3 position would be lost. To avoid this, hydrolysis of the lactone ring of the completely protected quinide is carried out before cleavage of the protective groups. In the case of the caffeoyl substituent, protection of its phenol functions has proved to be unnecessary because opening of the lactone ring of the quinide has not given rise to any isomerization.

In a third embodiment of the process according to the invention, 1,3- and 1,4-disubstituted derivatives of quinic acid are also prepared by selective esterification of the OH function in the 3 position of the quinide skeleton and, in the preparation of the corresponding quinic acids, by controlling the isomerization occurring between the 3 and 4 positions of the caffeoyl quinic acids.

To prepare the 1,3-O-dicaffeoyl derivatives, a reactive derivative of dicarbomethoxycaffeic acid, for example the acid chloride, is used in the selective esterification in the 3 position because, in this case, the carbonate previously used as a protective group for the phenol functions of the caffeic acid is not sufficiently soluble at the very low reaction temperature used of the order of −40° C.

In the case of the 1,4-O-dicaffeoyl derivatives, the selective esterification in the 3 position is carried out with trichloroethyl chloroformate as the protective group and the crude intermediate product is then directly used without purification by crystallization to avoid any rearrangement of the 3-carbotrichloroethoxy group into a 3,4-O-carbonyl group.

In a fourth embodiment relating to the preparation of the 3-O-caffeoyl-4-O-feruoyl derivatives, the above-mentioned selective esterification in the 3 position is again used to prepare the 3-O-caffeoyl starting derivative.

In these last two embodiments, the successive cleavage of the protective groups and, optionally, the hydrolysis of the quinides are carried out as described above in connection with the second embodiment.

In all the embodiments used, the compounds are prepared are obtained in very high yields because each step is completed without isomerization and the compounds may then readily be purified.

EXAMPLES

The invention is illustrated by the following Examples, in which parts and percentages are by weight, unless otherwise indicated.

The starting compounds and the reactants all come from Fluka AG. The solvents were made anhydrous before use. The medium pressure liquid chromatography (MPLC) was carried out using a Büchi chromatograph. The polyamide used for the chromatography was previously washed with methanol and then dried before use. The structure of the compounds was verified by nuclear magnetic resonance of the proton (NMR). The results of the elemental analyses, the yields and the melting points are shown.

Examples 1–3

1. Synthesis of 3-O-p-coumaroyl quinide and 3-O-p-coumaroyl quinic acid 1.1. 3,4-O-isopropylidene quinide A suspension of 66.2 g (344.4 mmol) and 2.1 g (11 mmol) p-toluene sulfonic acid in 900 ml acetone is refluxed for 24 h in a Soxhlet extractor containing 90 g 4 A° molecular sieve. After cooling to 0° C., 27 g (321.4 mmol) sodium bicarbonate are added. After the reaction mixture has been stirred for 1 h at the temperature of 0° C., the suspension is filtered and the solvent is evaporated. Recrystallization of the residue from a mixture of dichloromethane and hexane gives 67 g 3,4-O-isopropylidene quinide, melting point (Mp.) 141°–142° C., in a yield of 91%.

1.2. 1-O-carbotrichloroethoxy-3,4-O-isopropylidene quinide 34.96 g (165 mmol) trichloroethyl chloroformate diluted in 30 ml dichloromethane are added dropwise at 0° C. to a solution of 32.1 g (150 mmol) 3,4-O-isopropylidene quinide and 28.9 g (365 mmol) pyridine in 300 ml dichloromethane. After stirring at ambient temperature for 3 h, the reaction mixture is washed with an aqueous solution of 2N HCl and then with water, the solution is dried over sodium sulfate and the solvents are evaporated. Recrystallization of the residue from ethanol gives 49.5 g 1-O-carbotrichloroethoxy-3,4-O-isopropylidene quinide (Mp. 165°–166° C., yield 85%).

1.3. 1-O-carbotrichloroethoxy quinide

A solution of 39 g (100 mmol) 1-O-carbotrichloroethoxy-3,4-O-isopropylidene quinide in 60 ml of a 90% aqueous trichloroacetic acid solution is stirred for 3 3 h. After removal of the solvents, the residue is dissolved in 100 ml ethyl acetate, washed with a 2% aqueous sodium bicarbonate solution and then with brine and dried over sodium sulfate, followed by evaporation of the solvent. Recrystallization of the residue from toluene gives 24.6 g 1-O-carbotrichloroethoxy quinide (Mp. 130°–131° C., yield 70%). 1.4. 1-O-carbotrichloroethoxy-3-O-carbotrichloroethoxy-p-comaroyl quinide A solution of 8.95 g (25 mmol) carbotrichloroethoxy-p-coumaric acid chloride in 50 ml dichloromethane is added dropwise at −40° C. to a solution of 8.74 g (25 mmol) 1-O-carbotrichloroethoxy quinide and 2.18 g (27.5 mmol) pyridine in 100 ml dichloromethane. The reaction mixture is stirred for 24 h at −40° C. After removal of the solvents, the residue is dissolved in 100 ml ethyl acetate and the solution is washed successively with water, with an aqueous solution of 0.5N HCl and then with brine and dried over sodium sulfate, after which the solvents are removed by evaporation. Recrystallization of the residue from benzene gives 11.95 g 1-O-carbotrichlorethoxy-3-O-carbotrichloroethoxy-p-coumaroyl quinide (Mp. 154°–157° C., yield 71%). 1.5. 3-O-p-coumaroyl quinide 10.74 g (16 mmol) 1-O-carbotrichloroethoxy-3-O-carbotrichloroethoxy-p-coumaroyl quinide in 40 ml THF are treated with 40 ml acetic acid and 6.9 g (105 mmol) zinc powder with stirring for 3 h at ambient temperature. After evaporation of the solvents, 200 ml ethyl acetate are added to the residue which is then treated at 0° C. with an aqueous solution of 0.5N HCl. After separation, the organic phase is washed with an aqueous solution of 0.1N HCl and then with brine and is dried over sodium sulfate and the solvent is evaporated. Recrystallization of the residue from ethyl acetate gives 3.97 g 3-O-p-coumaroyl quinide (Mp. 240.5°–242.5° C., yield 78%); elemental analysis: calculated C 60.00, H 5.04; found C 59.79, H 5.30.

1.6. 3-O-p-coumaroyl quinic acid

A solution of 2.6 g (8.12 mmol) 3-O-p-coumaroyl quinide and 0.08 g (0.41 mmol) p-toluene sulfonic acid in 50 ml 50% aqueous THF is refluxed for 24 h. After removal of the solvents by evaporation, the residue is precipitated with a mixture of 1 volume THF to 10 volumes ether. Recrystallization of the precipitate from THF gives 1.95 g 3-O-p-coumaroyl quinic acid (Mp. 176°–178° C., yield 71%), elemental analysis: calculated C 56.80, H 5.49; found C 55.54, H 5,43.

2. Synthesis of 3-O-feruloyl quinide and 3-O-feruloyl quinic acid

Following the procedure described above in paragraph 1.4 to 1.6, the following compounds are successively obtained:

2.1.1-O-carbotrichloroethoxy-3-O-carbotrichloroethoxyferuloyl quinide (Mp. 102°–103.5° C., yield 77%); recrystallization from a mixture of acetone and water.

2.2.3-O-feruloyl quinide (Mp. 187.5°–190° C., yield 79%), elemental analysis: calculated C 58.29, H 5.18; found C 8.06, H 5.29.

2.3. 3-O-feruloyl quinic acid (yield 66%), elemental analysis: calculated C 55.43, H 5.47; found C 55.33, H 5.57; precipitation of the compound from a mixture of 1 volume THF to 5 volumes ether.

3. Synthesis of 3-O-caffeoyl quinide and 3-O-caffeoyl quinic acid 3.1. 1-O-carbotrichloroethoxy-3-dicarbomethoxycaffeoyl quinide A solution of 15.7 g (50 mmol) dicarbomethoxycaffeic acid chloride in 100 ml dichloromethane is added dropwise at −47° C. to a solution of 17.5 g (50 mmol) 1-O-carbotrichloroethoxy quinide and 4.35 g (55 mmol) pyridine in 200 ml dichloromethane. After the reaction mixture has been stirred for 24 h at −47° C., the solvents are removed by evaporation, the residue is dissolved in 230 ml ethyl acetate and the solution is successively washed with an aqueous solution of 0.5N HCl and with brine and is then dried over sodium sulfate and the solvents are evaporated. Purification of the residue by MPLC on polyamide using a mixture of 1 volume dichloromethane to 2 volumes hexane as eluent gives 24.69 g 1-O-carbotrichloroethoxy-3-dicarbomethoxycaffeoyl quinide (yield 79%).

3.2. 3-O-dicarbomethoxycaffeoyl quinide 16.58 g (26.42 mmol) 1-O-carbotrichloroethoxy-3-dicarbomethoxycaffeoyl quinide in 30 ml THF are treated with 60 ml acetic acid and 10.7 g (163.7 mmol) zinc powder with stirring for 2 h at ambient temperature. The residue is removed by filtration, after which the solvent is evaporated from the filtrate. After dissolution of the residue in 100 ml ethyl acetate and washing of the solution with an aqueous solution of 1N HCl and then with brine, the solution is dried over sodium sulfate and the solvent is evaporated. Taken up in a mixture of chloroform and hexane, the oily residue gives 11.53 g 3-O-dicarbomethoxycaffeoyl quinide in the form of an amorphous solid (yield 97%).

3.3. 3-O-caffeoyl quinide

A mixture of 11.53 g (26.42 mmol) 3-O-dicarbomethoxycaffeoyl quinide and 11.4 g (104.9 mmol) chlorotrimethyl silane in 75 ml pyridine is treated under reflux for 1 h. 12 g (282.3 mmol) LiCl are then added and the treatment under reflux is continued for 2 h. After removal of the solvents by evaporation, 100 ml ethyl acetate are added to the residue and the solution is successively washed with an aqueous solution of 1N HCl water and brine and dried over sodium sulfate and the solvent is evaporated. Recrystallization of the residue from ethyl acetate gives 5.35 g 3-O-caffeoyl quinide (Mp. 225°–229° C. with decomposition, yield 62%), elemental analysis: calculated C 57.14, H 4.80; found C 56.58, H 4.93.

3.4. 1,4-O-dicarbotrichloroethoxy-3-O-dicarbotrichloroethoxycaffeoyl quinide 5.33 g (66 mmol) pyridine and 14 g (66 mmol) trichloroethyl chloroformate are added dropwise to a suspension of 5.1 g (15.2 mmol) 3-O-caffeoyl quinide in 90 ml dichloromethane. After stirring for 24 h at ambient temperature, the solvents are removed by evaporation, 100 ml ethyl acetate are added to the residue, the solution is washed with an aqueous solution of 0.5N HCl and then with brine and dried over sodium sulfate and the solvent is evaporated. Recrystallization of the oily residue from a mixture of 1 volume dichloromethane to 3 volumes ethanol gives 10 g 1,4-O-dicarbotrichloroethoxy-3-O-dicarbotrichloroethoxycaffeoyl quinide (yield 63%).

3.5. 1,4-O-dicarbotrichloroethoxy-3-O-dicarbotrichloroethoxycaffeoyl quinic acid A mixture of 10 g (9.6 mmol) 1,4-O-dicarbotrichloroethoxy-3-O-dicarbotrichloroethoxycaffeoyl quinide is stirred for 5 days at ambient temperature in 65 ml THF and 8 ml concentrated HCl. After separation of the THF and saturation with NaCl, the aqueous phase is extracted with 3×40 ml ethyl acetate. The combined extracts are then washed with brine and dried over sodium sulfate and the solvent is evaporated. Treatment of the residue with a mixture of 1 volume dichloromethane to 10 volumes hexane gives 9.5 g 1,4-O-dicarbotrichloroethoxy-3-O-dicarbotrichloroethoxycaffeoyl quinic acid (yield 93%) in the form of an amorphous solid.

3.6. 3-O-caffeoyl quinic acid 1 g (0.94 mmol) 1,4-O-dicarbotrichloroethoxy-3-O-dicarbotrichloroethoxycaffeoyl quinic acid in 5 ml THF and 5 ml acetic acid is treated with 2.4 g (37.85 mmol) zinc powder for 2 h. After filtration of the precipitate, the filtrate is concentrated to dryness. The residue is then dissolved in 30 ml ethyl acetate, washed with cold 2N sulfuric acid saturated with NaCl and then with brine, the solution is dried over sodium sulfate and the solvent is evaporated. Treatment of the residue with a mixture of THF, ether and hexane in a ratio by volume of 1:10:10 followed by freeze-drying of the precipitate gives 0.24 g 3-O-caffeoyl quinic acid (yield 73%). Elemental analysis: calculated C 54.24, H 5.12; found C 53.60, H 5.00.

Examples 4–6

4. Synthesis of 4-O-p-coumaroyl quinide and 4-O-p-coumaroyl quinic acid 4.1. 1,3-O-dicarbotrichloroethoxy quinide (Mp. 127°-130° C., yield 67%) is prepared as described in paragraph 1.4 above by esterification of 1-O-carbotrichloroethoxyquinide with trichloroethyl chloroformate.

4.2. 1,3-O-dicarbotrichloroethoxy-4-O-carbotrichloroethoxy-p-coumaroyl quinide 3.58 g (10 mmol) carbotrichloroethoxy-p-coumaric acid chloride are added at 0° C. to a solution of 5.25 g (10 mmol) 1,3-O-dicarbotrichloroethoxy quinide and 0.8 g (10 mmol) pyridine in 25 ml dichloromethane. After stirring for 24 h at ambient temperature, the solvents are removed by evaporation. 70 ml ethyl acetate are then added to the residue, the solution is washed with an aqueous solution of 1N HCl and with brine and dried over sodium sulfate and the solvent is evaporated. Recrystallization of the residue from a solvent mixture of dichloromethane, ether and hexane in a ratio by volume of 1:5:5 gives 5.65 g 1,3-O-dicarbotrichloroethoxy-4-O-carbotrichloroethoxy-p-coumaroyl quinide (yield 67%).

4.3. Following the procedure described in paragraph 1.5 above, 4-O-p-coumaroyl quinide, elemental analysis: calculated C 60.00, H 5.04; found C 59.83, H 5.18, is obtained in a yield of 81% from 1,3-O-dicarbotrichloroethoxy-4-O-carbotrichloroethoxy-p-coumaroyl quinide.

4.4. Following the procedure described in paragraph 3.5 above, 1,3-O-dicarbotrichloroethoxy-4-O-carbotrichloroethoxy-p-coumaroyl quinic acid is obtained in a yield of 94% from 1,3-O-dicarbotrichloroethoxy-4-O-carbotrichloroethoxy-p-coumaroyl quinide.

4.5. 4-O-p-coumaroyl quinic acid

A solution of 5.62 g (6.5 mmol) 1,3-O-dicarbotrichloroethoxy-4-O-carbotrichloroethoxy-p-coumaroyl quinic acid in 15 ml THF and 65 ml acetic acid is treated with 12 g (189.2 mmol) zinc powder for 3 h at ambient temperature. After filtration of the precipitate, the filtrate is concentrated to dryness. 60 ml ethyl acetate are then added to the residue, the solution is washed with an aqueous solution of 1N HCl and then with brine and dried over sodium sulfate and the solvent is evaporated. Recrystallization of the residue from water gives 1.47 g 4-O-p-coumaroyl quinic acid (yield 67%), elemental analysis: calculated C 56.80, H 5.36; found C 56.74, H 5.39.

5. Synthesis of 4-O-feruloyl quinide and 4-O-feruloyl quinic acid

Following the procedure described above in paragraphs 4.1 to 4.5, the following compounds are successively prepared:

5.1. 1,3-dicarbotrichloroethoxy-4-O-carbotrichloroethoxyferuloyl quinide (yield 69%); final recrystallization of the residue from ethanol (see paragraph 4.2 above).

5.2. 4-O-feruloyl1 quinide (yield 66%), elemental analysis: calculated C 58.29, H 5.18; found C 58.06, H 5.36.

5.3. 1,3-O-dicarbotrichloroethoxy-4-O-carbotrichloroethoxyferuloyl quinic acid (yield 87%).

5.4. 4-O-feryloyl quinic acid (yield 64%), elemental analysis: calculated C 55.43, H 5.47; found C 55.39, H 5.42; washing of the solution of the precipitated residue dissolved in water with 3×50 ml ether followed by freeze drying.

6. Synthesis of 4-O-caffeoyl quinide and 4-O-caffeoyl quinic acid 6.1. 1,3-O-dicarbotrichloroethoxy-4-O-caffeoyl1 quinide 10.29 g (45.8 mmol) carbonylcaffeic acid chloride are added at −30° C. to a solution of 21.85 g (41.6 mmol) 1,3-O-dicarbotrichloroethoxy quinide in 150 ml dichloromethane, after which 3.8 g (48 mmol) pyridine diluted in 50 ml dichloromethane are added dropwise. After 1 h, the reaction mixture is left to return to ambient temperature and stirred for 24 h. After removal of the precipitate, the filtrate is concentrated to dryness. 400 ml ethyl acetate are then added to the residue, the solution is washed with an aqueous solution of 1N HCl and then with brine and the solvent is evaporated. The residue is then treated under reflux for 1 h in 500 ml 80% aqueous THF. After concentration to dryness, 500 ml THF are added and the undissolved precipitate is removed. After evaporation of the solvent from the filtrate, the residue is treated by flash chromatography in a polyamide column using a mixture of 1 volume dichloromethane to 2 volumes ethyl acetate as eluent, which gives 21.8 g 1,3-O-dicarbotrichloroethoxy-4-O-caffeoyl quinide (yield 76%) in the form of a white amorphous solid.

6.2. 4-O-caffeoyl quinide

4-O-caffeoyl quinide (Mp. 168°–172° C., yield 56%), elemental analysis: calculated C 57.14, H 4.80; found C 56.98, H 4.95, is obtained from 1,3-O-dicarbotrichloroethoxy-4-O-caffeoyl quinide in the same way as described in paragraph 4.3 above, except that the end product is recrystallized from a mixture of 1 volume ethyl acetate to 10 volumes chloroform.

6.3. 1,3-O-dicarbotrichloroethoxy-4-O-dicarbotrichloroethoxycaffeoyl quinide 7.9 g (37.2 mmol) trichloroethyl chloroformate diluted in 10 ml dichloromethane are added at 0° C. to a solution of 11.6 g (16.9 mmol) 1,3-O-dicarbotrichloroethoxy-4-O-caffeoyl quinide and 2.94 g (37.2 mmol) pyridine in 100 ml dichloromethane. After stirring at ambient temperature for 2 h, the reaction mixture is washed with an aqueous solution of 1N HCl and then with water and dried over sodium sulfate and the solvent is evaporated. Treatment of the residue with a solvent mixture of 1 volume dichloromethane to 10 volumes hexane gives 12.7 g 1,3-O-dicarbotrichloroethoxy-4-O-dicarbotrichloroethoxycaffeoyl quinide (yield 73%).

6.4. 1,3-O-dicarbotrichloroethoxy-4-O-dicarbotrichloroethoxycaffeoyl quinic acid A solution of 12.7 g (12.2 mmol) 1,3-O-dicarbotrichloroethoxy-4-O-dicarbotrichloroethoxycaffeoyl quinide in 870 ml THF is treated for 3 days with 9 ml concentrated HCl. After cooling to 0° C., the reaction mixture is adjusted to pH 2 by addition of solid sodium bicarbonate and is then saturated with NaCl. The organic phase is then separated and the aqueous phase is extracted with 2×20 ml ethyl acetate. After the combined organic phases have been dried over sodium sulfate, the solvents are evaporated. Treatment of the residue with a solvent mixture of THF and hexane in a ratio by volume of 1:20 gives 12.7 g 1,3-O-dicarbotrichloroethoxy- 4-O-dicarbotrichloroethoxycaffeoyl quinic acid in the form of an amorphous white powder (yield 99%)

6.5. 4-O-caffeoyl quinic acid

4-O-caffeoyl quinic acid (yield 45%) is prepared from 1,3-O-dicarbotrichloroethoxy-4-O-dicarbotrichloroethoxycaffeoyl quinic acid in the same way as described in paragraph 3.6 above, except that the final residue is dissolved in water and then washed with ether before freeze drying.

EXAMPLES 7-8

7. Synthesis of 1,3-O-dicaffeoyl quinide and 1,3-O-dicaffeoyl quinic acid 7.1. 1-O-caffeoyl-3,4-O-isopropylidene quinide 37.1 g (165 mmol) carbonyl caffeic acid chloride and 13.1 g (165 mmol) pyridine are successively added at 0° C. to a solution of 32.1 g (150 mmol) 3,4-O-isopropylidene quinide in 400 ml dichloromethane. After stirring for 24 h, the reaction mixture is washed with an aqueous solution of 1N HCl and then with water and dried over sodium sulfate and the solvents are evaporated. After the residue has been dissolved in 300 ml 60% aqueous THF, the residue is refluxed for 3 h. Evaporation of the solvents in vacuo, trituration with toluene and recrystallization of the residue from ethyl acetate gives 36.3 g 1-O-caffeoyl-3,4-O-isopropylidene quinide (yield 64%).

7.2. 1-O-dicarbotrichloroethoxycaffeoyl-3,4-O-isopropylidene quinide 44.9 g (212 mmol) trichloroethyl chloroformate diluted in 30 ml dichloromethane are added at 0° C. to a solution of 36.2 g (96.2 mmol) 1-O-caffeoyl-3,4-O-isopropylidene quinide and 16.7 g (212 mmol) pyridine in 250 ml dichloromethane. After stirring for 1 h at 0° C. and then for 1 h at ambient temperature, the reaction mixture is stirred with an aqueous solution of 1N HCl and then with water and dried over sodium sulfate and the solvents are evaporated. Washing of the residue with 400 ml of a mixture of ethyl acetate and hexane in a ratio by volume of 1:20 gives 67.5 g 1-O-dicarbotrichloroethoxycaffeoyl-3,4-O-isopropylidene quinide (yield 97%).

7.3. 1-O-dicarbotrichloroethoxycaffeoyl quinide

A solution of 59 g (81 mmol) 1-O-dicarbotrichloroethoxycaffeoyl-3,4-O-isopropylidene quinide in 500 ml 90% aqueous trifluoroacetic acid is stirred for 5 h. After evaporation of the solvents, 200 ml ethyl acetate are added to the residue, the solution is washed with brine and dried over sodium sulfate and the solvent is evaporated. Flash chromatography of the residue on polyamide using a mixture of equal volumes of dichloromethane and hexane as eluent gives 42.9 g 1-O-dicarbotrichloroethoxycaffeoyl quinide (yield 77%).

7.4. 1-O-dicarbotrichloroethoxycaffeoyl-3-O-dicarbomethoxycaffeoyl quinide 1.98 g (25 mmol) pyridine is added at −45° C. to a solution of 17.2 g (25 mmol) 1-O-dicarbotrichloroethoxycaffeoyl quinide in 200 ml dichloromethane, followed by the dropwise addition of 7.85 g (25 mmol) dicarbomethoxycaffeic acid chloride diluted in 20 ml dichloromethane. After stirring for 24 h at −45° C., the solvents are removed by evaporation in vacuo. 250 ml ethyl acetate are then added to the residue and the solution is washed with a cold aqueous solution of 1N HCl and then with brine, dried over sodium sulfate and the solvent is evaporated. Flash chromatography of the residue on polyamide using a mixture of dichloromethane and hexane in a ratio by volume of 1:2 as eluent gives 15.1 g 1-O-dicarbotrichloroethoxycaffeoyl-3-O-dicarbomethoxycaffeoyl quinide (yield 63%).

7.5. 1,3-O-dicaffeoyl quinide

A mixture of 13.7 g (14.2 mmol) 1-O-dicarbotrichloroethoxycaffeoyl-3-O-dicarbomethoxycaffeoyl quinide and 15.4 g (132 mmol) chlorotrimethyl silane in 140 ml pyridine is refluxed for 1 h. 12.3 g (284 mmol) LiCl are then added and the refluxing is continued for 30 minutes. After removal of the solvents, 200 ml ethyl acetate are added to the residue, the solution is washed with an aqueous solution of 1N HCl and then with brine, dried over sodium sulfate and the solvent is evaporated. Recrystallization of the residue from ethyl acetate gives 5 g 1,3-O-dicaffeoyl quinide (Mp. 185°–188° C., yield 71%), elemental analysis: calculated C 60.24, H 4.45; found C 60.43, H 4.32.

Following the procedure described in paragraphs 3.4 to 3.6 above, the following compounds are then successively prepared:

7.6. 1,3-O-bis-dicarbotrichloroethoxycaffeoyl-4-O-carbotrichloroethoxy quinide (yield 66%) by esterification of 1,3-O-dicaffeoyl quinide with trichloroethyl carbonate; recrystallization of the residue from ethanol (see 3.4).

7.7. 1,3-bis-dicarbotrichloroethoxycaffeoyl-4-O-carbotrichloroethoxy quinic acid (yield 92%); after treatment with concentrated HCl for 2 days, the reaction mixture is diluted with water and then treated with solid sodium bicarbonate at 0° C. to pH 4.8, saturated with NaCl and the aqueous phase is extracted with 3×10 ml THF instead of ethyl acetate and the desired product is obtained by treating the final residue with a mixture of THF and hexane in a ratio by volume of 1:25 (see 3.5).

7.8. 1,3-O-dicaffeoyl quinic acid (Mp. 227.5°–228.5° C., yield 60%), elemental analysis: calculated C 58.14, H 4.68, found C 58.14, H 4.72; recrystallization of the final residue from 5% aqueous acetic acid (see 3.6).

8. Synthesis of 1,4-O-dicaffeoyl quinide and 1,4-O-dicaffeoyl quinic acid

Following the procedure described in paragraph 7.4 above, 8.1. 1-O-dicarbotrichloroethoxycaffeoyl1-3-O-carbotrichloroethoxy quinide (obtained as a mixture of 23.3 g containing 20% of the starting 1-O-dicarbotrichloroethoxycaffeoyl quinide, as shown by NMR spectroscopic analysis and by thin layer chromatography) is prepared by reaction of 6.36 g (30 mmol) trichloroethyl chloroformate with 20.61 g (30 mmol) 1-O-dicarbotrichloroethoxycaffeoyl quinide.

8.2. 4-O-caffeoyl3-O-carbotrichloroethoxy-1-O-dicarbotrichloroethoxycaffeoyl quinide 22 g of the solid mixture of paragraph 8.1 above in 200 ml dichloromethane are treated by the successive addition at −10° C. of 8.2 g (36.5 mmol) carbonylcaffeic acid chloride and 3.6 g (45 mmol) pyridine. After stirring for 24 h at −10° C., the solvents are removed by evaporation. 200 ml ethyl acetate are then added to the residue, the solution is washed with an aqueous solution of 0.5N HCl and then with brine and the solvent is evaporated in vacuo. The residue is then dissolved in 100 ml 20% aqueous THF and the solution is refluxed for 90 minutes. After concentration to dryness, 200 ml ethyl acetate are added, the solution is washed with brine and dried over sodium sulfate and the solvent is removed by evaporation. MPLC of the residue on polyamide using a mixture of dichloromethane and hexane in a ratio by volume of 1:2 as eluent gives 11.5 g 4-O-caffeoyl-3-O-carbotrichloroethoxy-1-O-dicarbotrichloroethoxycaffeoyl quinide (yield 38% for the two steps 8.1 and 8.2).

8.3. 1,4-O-dicaffeoyl quinide

A solution of 4.1 g (4 mmol) 4-O-caffeoyl-3-O-carbotrichloroethoxy-1-O-dicarbotrichloroethoxycaffeoyl quinide in 10 ml THF and 15 ml acetic acid is treated for 3 h with 5.07 g (80 mmol) zinc powder. After elimination of the solvents, 20 ml ethyl acetate are added to the residue, the solution is washed with a cold solution of 0.5N HCl and then with brine, dried over sodium sulfate and the solvent is evaporated. Treatment of the crude product with a solvent mixture of ethyl acetate and chloroform in a ratio by volume of 1:10 followed by freeze drying of the residue gives 1.38 g 1,4-dicaffeoyl quinide (yield 69%), elemental analysis: calculated C 60.24, H 4.45; found C 60.56, H 4.25.

8.4. 4-O-caffeoyl-3-O-carbotrichloroethoxy-1-O-dicarbotrichloroethoxycaffeoyl quinic acid A solution of 7 g (6.83 mmol) 4-O-caffeoyl-3-O-carbotrichloroethoxy-1-O-dicarbotrichloroethoxycaffeoyl quinide in 30 ml THF is treated with 5 ml concentrated HCl for 3 days. After the reaction mixture has been diluted with 10 ml water, it is treated with sodium bicarbonate to pH 4 at 0° C. After saturation with NaCl the organic phase is separated. The aqueous phase is extracted with 3×15 ml ethyl acetate. The combined organic phases are then washed with brine and dried over sodium sulfate and the solvents are evaporated. Recrystallization of the residue from a solvent mixture of THF, ether and hexane in a ratio by volume of 1:5:20 gives 6.28 g 4-O-caffeoyl-3-O-carbotrichloroethoxy-1-O-dicarbotrichloroethoxycaffeoyl quinic acid (yield 88%).

8.5. 1,4-O-dicaffeoyl quinic acid

A solution of 2.09 g (2 mmol) 4-O-caffeoyl-3-O-carbotrichloroethoxy-1-O-dicarbotrichloroethoxycaffeoyl quinic acid in 10 ml THF and 10 ml acetic acid is treated with 2.5 g (40 mmol) zinc powder for 2 h. After removal of the solvents, 50 ml ethyl acetate are added to the residue which is then treated with a 2N aqueous sulfuric acid solution at 0° C. After saturation with NaCl the ethyl acetate is separated and the aqueous phase is extracted with 3×10 ml ethyl acetate. The combined organic phases are then washed with a cold 2N aqueous sulfuric acid solution and then with brine, dried over sodium sulfate and the solvent is evaporated. MPLC of the residue on silica gel using a solvent mixture of n-butanol, ethanol and water in a ratio by volume of 6:1:0.5 as eluent, followed by freeze drying, gives 0.74 g of a mixture containing 95% 1,4-O-dicaffeoyl quinic acid and 5% 1,3-O-dicaffeoyl quinic acid (yield 72%), as verified by NMR spectroscopy.

Example 9

Synthesis of 3-O-caffeoyl1-4-O-feruloyl quinide and 3-O-caffeoyl-4-O-feruloyl quinic acid 9.1. 1-O-carbotrichloroethoxy-4-O-carbotrichloroethoxyferuloyl-3-O-dicarbomethoxycaffeoyl quinide 10.7 g (27.2 mmol) carbotrichloroethoxyferulic acid chloride and 2.17 g (27.2 mmol) pyridine are successively added at −10° C. to a solution of 15.7 g (25 mmol) 1-O-carbotrichloroethoxy-3-O-dicarbomethoxycaffeoyl quinide in 150 ml dichloromethane. After stirring for 24 h at 0° C., the reaction mixture is washed with an aqueous solution of 1N HCl and then with water and dried over sodium sulfate and the solvents are evaporated. MPLC of the residue on polyamide using a solvent mixture of dichloromethane and hexane in a ratio by volume of 1:4 as eluent, followed by recrystallization from a mixture of the same solvents in a ratio by volume of 1:20, gives 14.4 g 1-O-carbotrichloroethoxy-4-O-carbotrichloroethoxyferuloyl-3-O-dicarbomethoxycaffeoyl quinide (yield 60%).

9.2. 3-O-dicarbomethoxycaffeoyl1-4-O-feruloyl quinide

A solution of 5.6 g (5.7 mmol) 1-O-carbotrichloroethoxy-4-O-carbotrichloroethoxyferuloyl-3-O-dicarbomethoxycaffeoyl quinide in 55 ml THF and 55 ml acetic acid is treated with 3.7 g (57.4 mmol) zinc powder for 2 h. After removal of the solvents, 50 ml dichloromethane are added and the solution is washed with a 0.5N aqueous HCl solution and then with water and is dried over sodium sulfate and solvent is evaporated. Treatment of the residue with a solvent mixture of dichloromethane and hexane in a ratio by volume of 1:10 gives 3.22 g 3-O-dicarbomethoxycaffeoyl-4-O-feruloyl quinide (yield 90%). 9.3. 3-O-caffeoyl1-4-O-feruloyl quinide A suspension of 4.5 g (106 mmol) LiCl and 2.74 g (4.4 mmol) 3-O-dicarbomethoxycaffeoyl-4-O-feruloyl quinide is refluxed for 1 h in 30 ml pyridine. After removal of the solvent, 100 ml ethyl acetate are added to the residue, the solution is washed with an aqueous solution of 0.5N HCl and then with brine and dried over sodium sulfate and the solvent is evaporated. Treatment of the residue with a solvent mixture of dichloromethane and hexane in a ratio by volume of 1:10 gives 1.44 g 3-O-caffeoyl-4-O-feruloyl quinide (yield 64%), elemental analysis: calculated C 60.94, H 4.72; found C 61.10, H 4.48.

9.4. 3-O-caffeoyll-4-O-feruloyl quinic acid

A solution of 0.84 g (1.64 mmol) 3-O-caffeoyl -4-O-feruloyl quinide in 20 ml 50% aqueous acetonitrile containing 10 drops trifluoroacetic acid is refluxed for 24 h. After removal of the solvent, 50 ml ethyl acetate are added to the residue, the solution is washed with brine and dried over sodium sulfate and the solvent is eliminated by evaporation. Treatment of the residue with a solvent mixture of ethyl acetate and hexane in a ratio by volume of 1:5, followed by freeze drying, gives 0.44 g 3-O-caffeoyl -4-O-feruloyl quinic acid (yield 51%), elemental analysis: calculated C 58.87, H 4.94; found C 59.07, H 4.96.

I claim:

1. A process for the production of 3- and/or 4-substituted quinic acid derivatives, in which the substituent in the 3 position is different from the substituent in the 4 position and in which a derivative of a hydroxycinnamic acid, of which the hydroxyl group(s) is/are protected, is reacted with a protected derivative of quinic acid to form an ester and the protective groups are subsequently cleaved, characterized in that the quinic acid derivative used is a quinide, in that the esterification or the introduction of a protective group in the case of the 4-substituted derivatives is carried out regioselectively in the 3 position of the quinic acid skeleton at a temperature below $-10°$ C., in that the protective groups are cleavable under controlled acidity and temperature conditions and in that, when it is desired to prepare the final quinic acid, the quinide is subjected to acidic hydrolysis under controlled conditions, the controlled conditions enabling any degradation or isomerization to be avoided.

2. A process as claimed in claim 1 for the production of monosubstituted 3-O-hydroxycinnamoyl derivatives, characterized in that the OH functions in the 3, and 4 positions of the quinide acid are protected by reaction with acetone which leads to 3,4-O-isopropylidene quinide, in that a protective carbonate group is introduced into the 1 position, in that the OH functions in the 3 and 4 positions are released, in that the 3 position is selectively esterified by carrying out esterification at a temperature below $-10°$ C. with a reactive derivative of a hydroxycinnamic acid of which the phenol function(s) has/have been protected.

3. A process as claimed in claim 2 for the production of 3-O-p-coumaroyl or 3-O-feruloyl derivatives, characterized in that the protective group of the phenol function is trichloroethyl carbonate, in that the acetonide group protecting the 3 and 4 positions is released with aqueous trifluoroacetic acid at ambient temperature and in that the trichloroethyl carbonate is cleaved with zinc in acetic medium at ambient temperature.

4. A process as claimed in claim 2 for the production of 3-O-caffeoyl derivatives, characterized in that the protective group of the phenol functions is methyl carbonate, in that the acetonide group protecting the 3 and 4 positions is released with aqueous trifluoroacetic acid at ambient temperature and in that the protective trichloroethyl carbonate group is released with zinc in the presence of acetic acid and the methyl carbonate groups are released with lithium chloride in the presence of chlorotrimethyl silane in pyridine.

5. A process as claimed in claim 1 for the production of 4-O-hydroxycinnamoyl derivatives, characterized in that the 1 and 3 functions of a quinide are protected with trichloroethyl carbonate groups, in that the 4 position is esterified with a reactive derivative of a hydroxycinnamoyl acid of which the phenol function(s) has/have been protected and in that the groups protecting the 1 and 3 positions are cleaved.

6. A process as claimed in claim 1 for the production of 1,3-O- and 1,4-O-disubstituted derivatives, characterized in that, the 3 and 4 positions having been protected, the 1 position is esterified with a reactive derivative of a protected hydroxycinnamoyl acid, the 3 and 4 positions are released, the 3 position is esterified with a reactive derivative of a protected hydroxycinnamoyl acid in the production of the 1,3-O-disubstituted derivatives and, in the production of the 1,4-O-disubstituted derivatives, the 3 position is protected with carbonate before esterification in the 4 position with a reactive derivative of a protected hydroxycinnamic acid.

7. A process as claimed in claim 2 for the production of 3,4-O-disubstituted derivatives, characterized in that, after the 1 position of the quinide has been protected, the 3 position and then the 4 position are esterified with a reactive derivative of a hydroxycinnamic acid of which the phenol functions have been protected.

8. A process as claimed in any of claims 1 to 7, characterized in that the quinide is converted into quinic acid by controlled acidic hydrolysis with concentrated hydrochloric acid at low temperatures in the presence of a polar solvent.

9. A process as claimed in claim 8 for the production of a caffeoyl quinic acid, characterized in that hydrolysis of the lactone ring of the completely protected quinide is carried out before cleavage of the protective groups.

* * * * *

UNITED STATES PATENT AND TRADEMARK OFFICE
CERTIFICATE OF CORRECTION

PATENT NO. : 5,401,858
DATED     : March 28, 1995
INVENTOR(S) : Tuong Huynh-Ba

It is certified that error appears in the above-indentified patent and that said Letters Patent is hereby corrected as shown below:

Title page, item [54] in the Title, "OUNIC" should be --QUINIC--.

Column 1, line 3, "OUNIC" should be --QUINIC--.

Column 14, line 38 (line 1 of claim 7), "2" should be --1--.

Signed and Sealed this

Thirtieth Day of May, 1995

Attest:

BRUCE LEHMAN

*Attesting Officer*         *Commissioner of Patents and Trademarks*